United States Patent [19]

Crawford

[11] Patent Number: 5,366,441
[45] Date of Patent: Nov. 22, 1994

[54] CATHETER INTRODUCER ASSEMBLY WITH GUIDEWIRE

[75] Inventor: Mark A. Crawford, Sandy, Utah

[73] Assignee: Becton, Dickinson and Company, Franklin Lakes, N.J.

[21] Appl. No.: 127,725

[22] Filed: Sep. 28, 1993

[51] Int. Cl.⁵ .......................................... A61M 5/178
[52] U.S. Cl. .................................. 604/53; 604/164; 604/159
[58] Field of Search ................ 604/165, 164, 53, 168, 604/264, 52, 159

[56] References Cited

U.S. PATENT DOCUMENTS

| | | | |
|---|---|---|---|
| Re. 34,086 | 10/1992 | George | 128/200.26 |
| 3,595,230 | 7/1971 | Suyeeka | 128/214.4 |
| 3,682,173 | 8/1972 | Center | 128/214.4 |
| 3,757,771 | 9/1973 | Ruegg et al. | 128/2.1 |
| 4,068,659 | 1/1978 | Moorehead | 128/214.4 |
| 4,205,675 | 6/1980 | Vaillancourt | 128/214.4 |
| 4,326,520 | 4/1982 | Alley | 128/214.4 |
| 4,417,886 | 11/1983 | Frankhouser | 604/53 |
| 4,525,157 | 6/1985 | Vaillancourt | 604/165 |
| 4,652,256 | 3/1987 | Vaillancourt | 604/52 |
| 4,655,750 | 4/1987 | Vaillancourt | 604/165 |
| 4,772,264 | 9/1988 | Cragg | 604/158 |
| 4,894,052 | 1/1990 | Crawford | 604/63 |
| 5,129,887 | 7/1992 | Euteneuer et al. | 604/165 |
| 5,158,544 | 10/1992 | Weinstein | 604/164 |
| 5,246,426 | 9/1993 | Lewis et al. | 604/164 |

Primary Examiner—John G. Weiss
Attorney, Agent, or Firm—Michael G. Schwartz; Eric M. Lee

[57] ABSTRACT

A catheter introducer assembly is disclosed. The catheter introducer assembly is made UP of a housing having a needle attached to it. A guidewire is slidably located within the lumen of the needle. A catheter assembly is mounted over the needle. Within the housing is a plunger and secured to the plunger is a retainer for releasably retaining the guidewire within the needle lumen. Axial movement of the plunger causes axial movement of the guidewire. The retainer releasably retains the guidewire. Also disclosed is a method of introducing a catheter into a blood vessel. The method involves the steps of piercing the blood vessel with a sharp needle having a catheter mounted axially on it; sliding a guidewire through the lumen of the needle so that the guidewire protrudes from the distal end of the needle and into the vessel; sliding the catheter over the guidewire and into the vessel; withdrawing the needle from the catheter; and retaining the guidewire within the catheter after withdrawal of the needle.

16 Claims, 4 Drawing Sheets

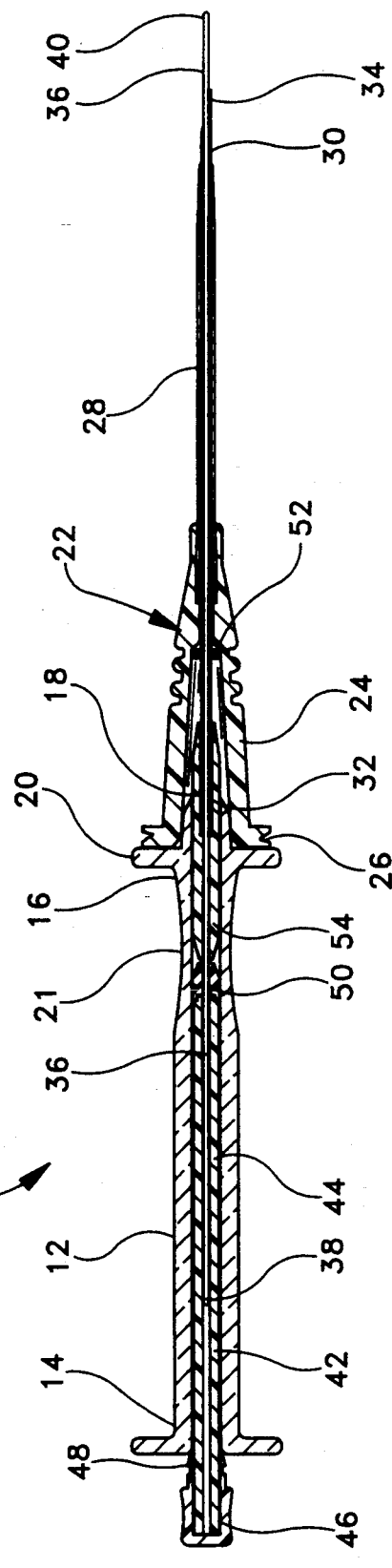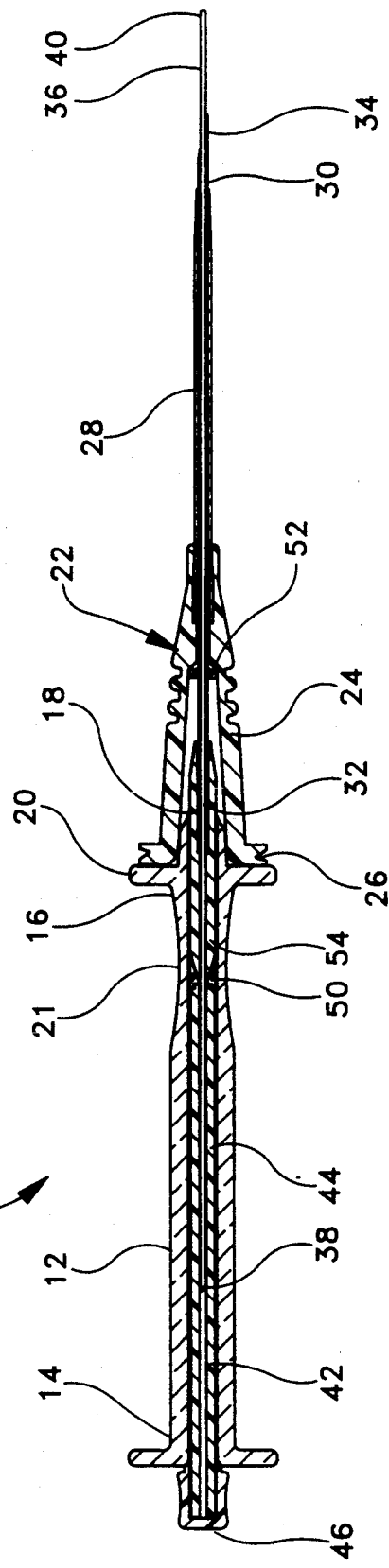

CATHETER INTRODUCER ASSEMBLY WITH GUIDEWIRE

BACKGROUND

This invention relates to the field of medical catheters. Specifically, it relates to an intra vascular catheter introducer with a guidewire to assist in the introduction of a catheter into a blood vessel such as a vein or an artery.

Intravascular catheters are used in the medical arts for infusing fluids into a patient or drawing fluids from a patient or monitoring physiological parameters such as blood pressure. They may also be used to introduce and locate probes such as blood pressure or blood gas probes. Conventional catheters such as the Insyte ® catheter available from Beeton Dickinson and Co. of Franklin Lakes, N.J. are typically used for intravenous applications. Such catheters are less suited to intra-arterial applications due to the anatomy of arteries which makes the introduction of catheters difficult. For this reason, various catheters have been invented which make the introduction of a catheter into an artery less difficult. An example of such a device is the Arrow ® Radial Artery Catheterization set available from Arrow International, Inc. of Reading Penna. and described in U.S. Pat. No. 4,417,886. A further example is the device of U.S. Pat. No. 4,894,052 to Becton Dickinson and Company of Franklin Lakes, N.J. Both patents are incorporated herein by reference.

SUMMARY OF THE INVENTION

The invention is a catheter introducer set made up of a hollow housing having an axial lumen, a proximal end and a distal end. A needle hub is secured to the distal end of the housing. A needle having an axial lumen, a proximal end and a distal end, the proximal end is mounted to the needle hub. Slidably located axially within the lumen of the needle is a guidewire. A catheter assembly is slidably located axially over the needle. A plunger having a proximal end and a distal end is slidably located axially within the lumen of the housing. The catheter introducer also has a retaining means for releasably retaining the guidewire in the needle lumen. Axial movement of the plunger causes axial movement of the guidewire. The retaining means is adapted to be moveable between a first position in which the guidewire is secured to the plunger and a second position in which the guidewire is released from the plunger.

The invention also includes a method of introducing a catheter into a blood vessel. The method involves the steps of piercing the blood vessel with a sharp needle having a catheter mounted axially on it; sliding a guidewire through the lumen of the needle so that the guidewire protrudes from the distal end of the needle and into the vessel; sliding the catheter over the guidewire and into the vessel; withdrawing the needle from the catheter; and, retaining the guidewire within the catheter after withdrawing the needle.

BRIEF DESCRIPTION OF THE DRAWINGS

FIG. 3 is a cross-sectional view of the device showing the position of the guidewire when the catheter is introduced into a blood vessel.

FIG. 4 is a cross-sectional view of the device showing the plunger and guidewire disengaged;

DETAILED DESCRIPTION

Figure 1:
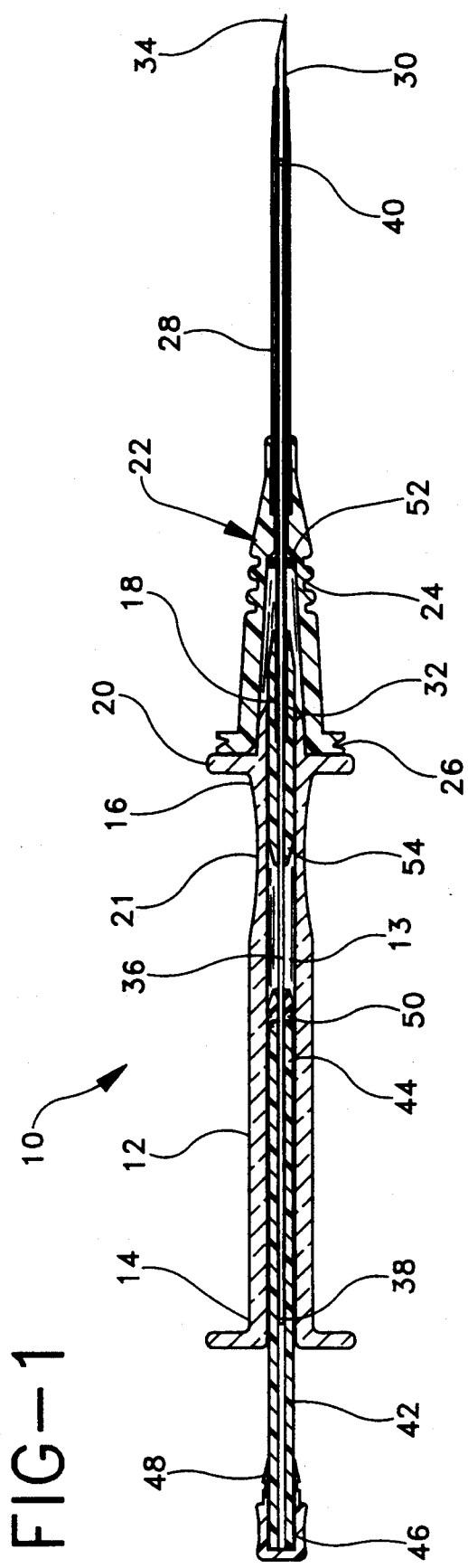
FIG. 1 is a cross-sectional view of the device with the plunger and guidewire engaged.

Catheter introducer set 10 is shown in FIG. 1. Hollow cylindrical housing 12 has proximal end 14, distal end 16 and lumen 13. Distal end 16 is provided with generally frusto-conical needle hub 18 to which is secured needle 30. Adjacent distal end 16 is generally circumferential flange 20. Proximal of flange 20, housing 12 has a region of reduced diameter 21 to facilitate the gripping of housing 12 between the fingers of a user. Needle 30 has proximal end 32 secured to hub 18 and a sharp distal end 34. Distal end 34 is designed to pierce the blood vessel into which the catheter is to be introduced. Needle 30 has lumen 31. Needle 30 is provided with notch 54, which extends through wall 33 of needle 30 to lumen 31, the purpose of which will be explained.

Figure 2:
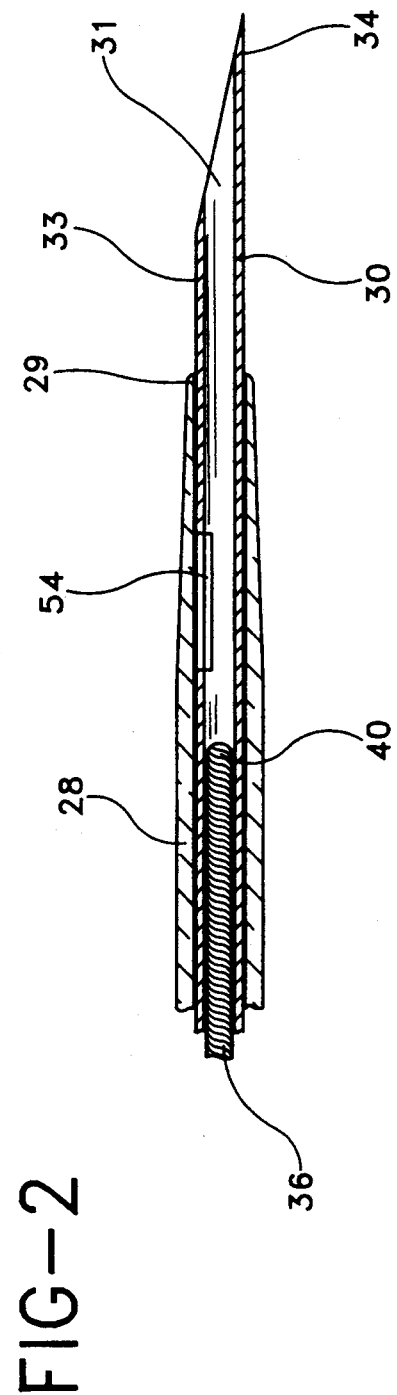
FIG. 2 is a detailed cross-sectional view of part of the device showing the notch in the needle and the guidewire.

Catheter assembly 22 is placed on needle hub 18. Catheter assembly 22 comprises adapter 24 and cannula 28. Adapter 24 is provided with a luer connector 26 which fits over needle hub 18 and abuts flange 20 as shown in FIG. 1. Catheter cannula 28 fits concentrically around needle 30 so that catheter 28 can slide off needle 30. Annular space 29 is formed between cannula 28 and needle 30 (see FIG. 2). Luer connector 26 has an interior cavity 27. Within cavity 27 is blood seal 52. Blood seal 52 is preferably an O-ring which fits snugly around needle 30.

Guidewire 36 fits axially within lumen 31 of needle 30. It has proximal end 38 and distal end 40. Guidewire 36 is approximately the combined length of housing 12 and needle 30. Releasably secured to guidewire 36 is plunger 42. Plunger 42 fits axially into lumen 13 of housing 12. Plunger 42 has a proximal end 46 and a distal end 44. Secured to distal end 44 is an elastomeric retainer 50 which releasably secures plunger 42 to guidewire 36. Plunger 42 fits co-axially over guidewire 38 as shown in FIG. 1. Retainer 50 and guidewire 38 are dimensioned such that when guidewire 38 is in the position shown in FIG. 1, its outer surface 39 radially presses against inner surface 51 of retainer 50 due to the elasticity of retainer 50. Guidewire 38 is thus held in position in plunger 42 such that when plunger 42 slides in and out of housing 12, guidewire 38 slides with it. At the proximal end 46 of plunger 42 is a seal 48 which insures that when plunger 42 is in the fully advanced position shown in FIG. 4, a seal is formed between the proximal end 14 of housing 12 and the proximal end 46 of plunger 42.

Figure 6:
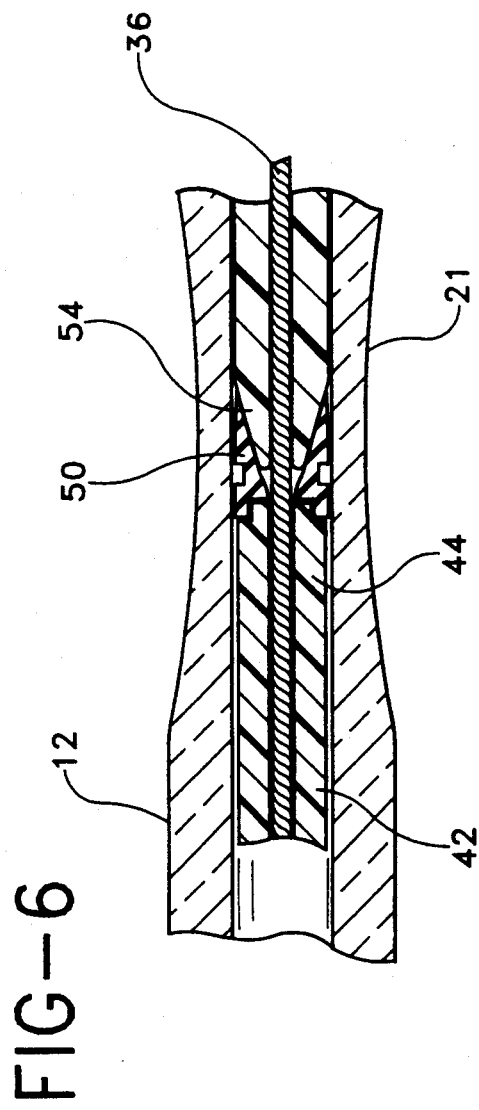
FIG. 6 is a detailed cross-sectional view of the plunger on disengagement of the guidewire.

Frusto-conical member 54 is provided proximal of hub 18 and within lumen 13 of housing 12 to release retainer 50 from guidewire 36 in a manner discussed below and shown in FIG. 6. Frusto-conical member 54 is coaxial with housing 12 and projects in the proximal direction.

Catheter introducer 10 is used as follows. The practitioner locates the blood vessel into which catheter 22 is to be introduced. The practitioner pierces the blood vessel by means of sharp tip 34 of needle 30. If the blood vessel has been correctly located, blood will appear in annular space 29 between catheter cannula 28 and needle 30 since blood will travel from lumen 31 of needle 30 and through notch 54. In addition, blood will travel up lumen 31 of needle 30 and towards lumen 13 of cylindrical of housing 12. Seal 48 prevents this blood from escaping. Guidewire 36 partially occludes the flow of blood through lumen 31. Blood in annular space 29 also travels towards cavity 27 of catheter adapter 24. Seal 52 prevents this blood from escaping further into adapter 24.

Figure 5:
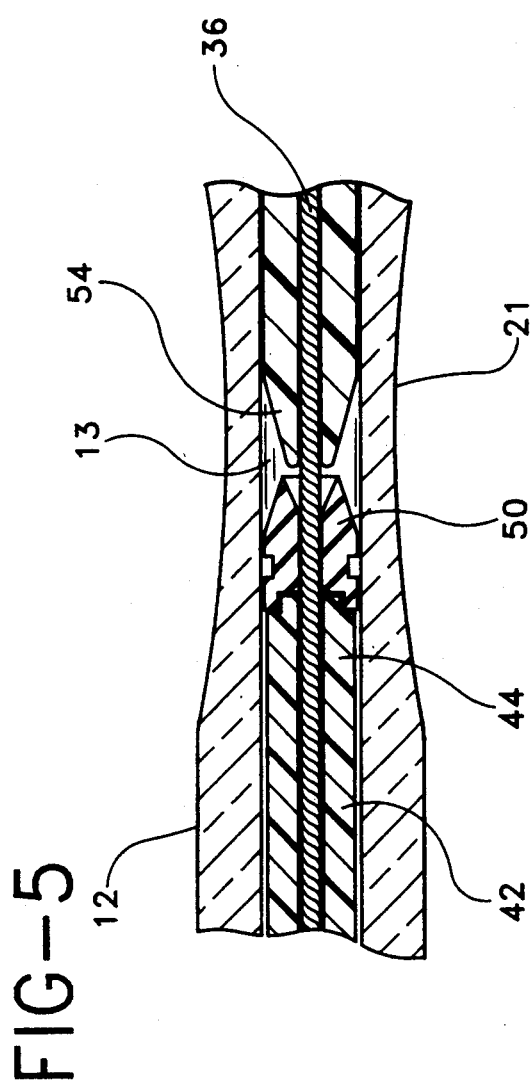
FIG. 5 is a detailed cross-sectional view of the plunger just prior to disengagement of the guidewire.
Figure 7:
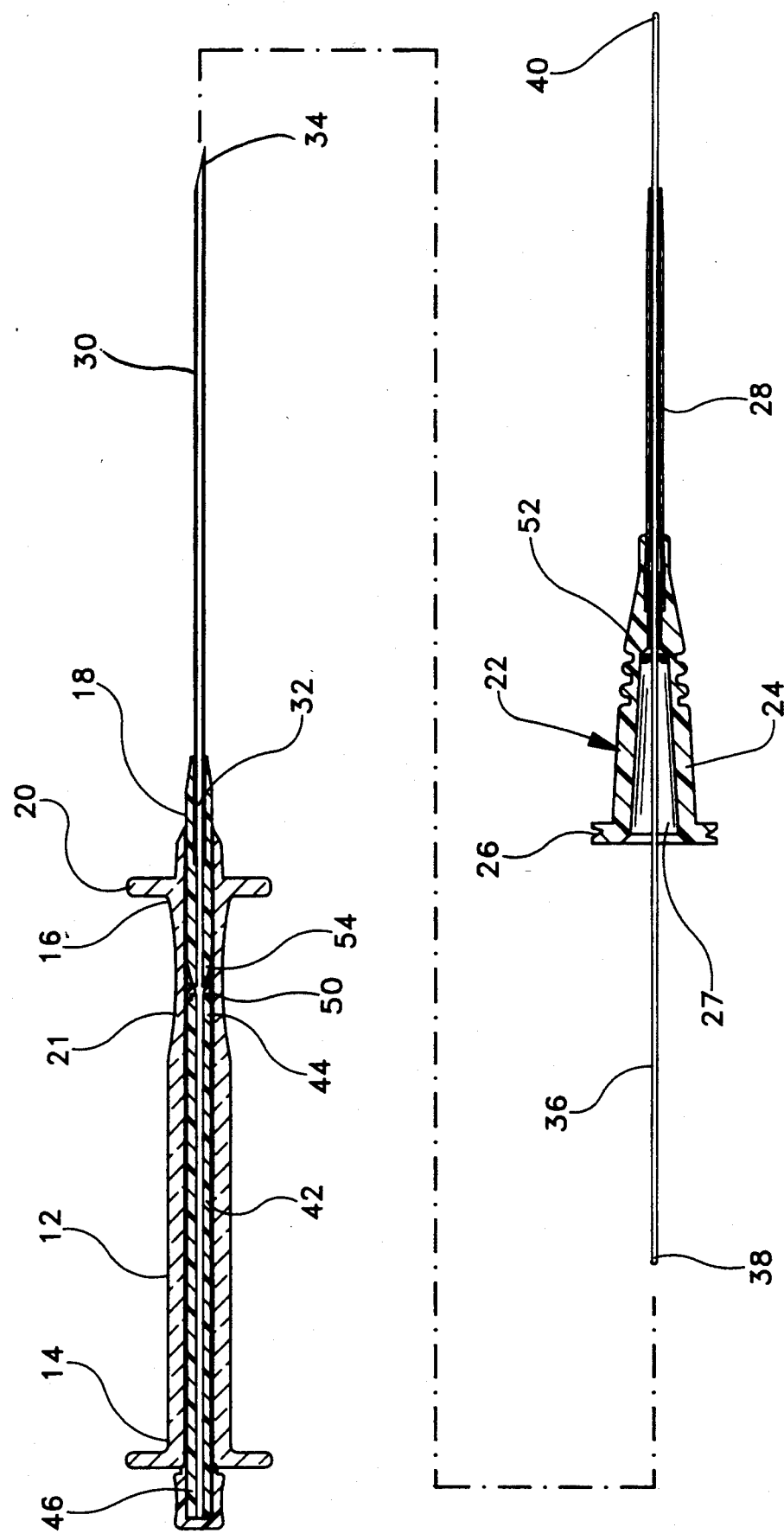
FIG. 7 is a cross-sectional view of the device after introduction of the catheter into a blood vessel, showing the needle and housing withdrawn from the catheter and the guidewire remaining in the catheter.

Once needle 30 has been successfully introduced into the blood vessel, plunger 42 is moved in the distal direction, thereby introducing guidewire 36 into the vessel through lumen 31 of needle 30. This step is shown in FIGS. 3 and 5. On full movement of plunger 42 into housing 12, retainer 50 will impinge upon conical member 54 as shown in FIGS. 4 and 6. Conical member 54 will spread retainer 50 as shown in FIG. 5, thereby relieving the radial force between the guidewire 36 and retainer 50 and releasing guidewire 36 from retainer 50. Guidewire 36 is thus free to move axially within the lumen of the needle. At this point, catheter assembly 22 can be threaded over guidewire 36 and fully introduced into the blood vessel. Once catheter 22 has been introduced into the blood vessel, housing 12 and thus needle 30 are removed from the catheter as shown in FIG. 7. Guidewire 36 remains within the lumen of catheter 22, thereby reducing the flow of blood out of catheter 24 into cavity 27 of catheter adapter 24. Seal 52 prevents blood from escaping from cavity 27.

While the description of this invention is with reference to a preferred embodiment, it is not intended to be limiting. Its scope is to be determined by the claims and their equivalents.

I claim:

1. A catheter introducer set comprising:
   a hollow housing having an axial lumen, a proximal end and a distal end;
   a needle hub at the distal end of the housing;
   a needle having an axial lumen, a proximal end and a distal end, the proximal end being secured to the needle hub;
   a guidewire slidably located axially within the lumen of the needle;
   a catheter assembly slidably located axially over the needle, the catheter assembly including a catheter adapter;
   a plunger slidably located axially within the lumen of the housing, the plunger having a proximal end and a distal end; and
   retaining means for releasably retaining the guidewire within the needle lumen such that axial movement of the plunger causes axial movement of the guidewire, the retaining means being adapted to be moveable between a first position in which the guidewire is secured to the plunger and a second position in which the guidewire is released from the plunger.

2. The catheter introducer set of claim 1 wherein the retaining means is mounted at the distal end of the plunger.

3. The catheter introducer set of claim 1 further comprising means in the housing for engaging the retaining means thereby moving the retaining means from the first position into the second position.

4. The catheter introducer set of claim 2 wherein the retaining means comprise an annular member which is radially compressed by the guidewire when the retaining means is in the first position.

5. The catheter introducer set of claim 4 further comprising means for engaging the retaining means to move the retaining means into the second position such that in the released position the retaining means is no longer radially compressed by the guidewire.

6. The catheter introducer set of claim 1 further comprising a seal between the catheter adapter and the guidewire.

7. The catheter introducer set of claim 1 further comprising a seal between the plunger and the housing.

8. A catheter introducer set for introducing a catheter into a blood vessel, the catheter introducer set comprising:
   a housing defining a housing lumen;
   a needle hub on the housing;
   a needle having a proximal end attached to the needle hub, a distal end and a lumen;
   a catheter assembly having a cannula and an adapter and said catheter assembly mounted axially on the needle;
   a guidewire slidably located axially in the needle lumen;
   means disposed inside the housing lumen for retaining the guidewire within the needle lumen by applying a releasable radial force to the guidewire while the needle is being inserted into the vessel; and
   means for releasing the guidewire from the means for retaining once the needle has been inserted into the blood vessel such that while the needle is being removed from the cannula, the guidewire remains in the catheter assembly.

9. The catheter introducer set of claim 8 further comprising a seal between the catheter adapter and the guidewire.

10. The catheter introducer set of claim 8 wherein the means for releasing is secured to the housing, the means for releasing being adapted to release the guidewire from the means for retaining on introduction of the guidewire into the vessel.

11. The catheter introducer set of claim 8 further comprising a plunger slidable in the housing and the means for retaining being secured to the plunger such that the guidewire is slidable with the plunger and the guidewire can be introduced into the vessel by sliding the plunger in a distal direction.

12. The catheter introducer set of claim 11 further comprising a seal between the plunger and the housing.

13. The catheter introducer set of claim 8 wherein the means for releasing is secured to the housing.

14. A method of introducing a catheter into a blood vessel comprising the steps of:
   piercing the blood vessel with a sharp needle, the needle having a proximal end, a distal end and an axial lumen, the needle further having a catheter mounted axially on the needle and being mounted to a needle hub;
   sliding a guidewire through the lumen of the needle so that the guidewire protrudes from the distal end of the needle and into the vessel;
   sliding the catheter over the guidewire and into the vessel;
   withdrawing the needle from the catheter; and retaining the guidewire within the catheter while withdrawing the needle.

15. The method of claim 14 further comprising the step of retaining the guidewire slidably within the needle during the step of piercing the blood vessel.

16. The method of claim 15 further comprising the step of releasing the guidewire on withdrawal of the needle.

* * * * *